United States Patent [19]

Meister et al.

[11] Patent Number: 5,099,852
[45] Date of Patent: Mar. 31, 1992

[54] METHOD FOR DETERMINING THE ARTERIAL BLOOD PRESSURE IN A NON-INVASIVE MANNER

[75] Inventors: Jean J. Meister, Epalinges; Yanik Tardy, Lausanne, both of Switzerland

[73] Assignee: Asulab S.A., Bienne, Switzerland

[21] Appl. No.: 489,038

[22] Filed: Mar. 6, 1990

[30] Foreign Application Priority Data

Mar. 8, 1989 [CH] Switzerland .......................... 856/89-6

[51] Int. Cl.$^5$ .............................................. A61B 5/02
[52] U.S. Cl. ................................ 128/672; 128/661.08; 128/691
[58] Field of Search ...................... 128/660.02, 661.04, 128/661.05, 661.1, 661.08, 661.09, 672, 691; 73/861.25

[56] References Cited

U.S. PATENT DOCUMENTS 4,425,920 1/1984 Bourland et al. .................... 128/672
4,562,843 1/1986 Djordjerich et al. ................ 128/672

OTHER PUBLICATIONS

International Conference on Biomedical Transducers, vol. 1, 11/3/75, pp. 271-276.

Medical and Biological Engineering and Computing, vol. 25, No. 2, Mar. 1987, pp. 189-194.

Primary Examiner—Stephen C. Pellegrino
Assistant Examiner—Steven J. Shumaker
Attorney, Agent, or Firm—Griffin Branigan & Butler

[57] ABSTRACT

This method for establishing blood pressure in an artery employs the measurement results from two non-invasive sensors (5, 6) of artery diameter at two closely spaced locations (3, 4) separated by a distance $\Delta x$. The method provides for measuring the time spread $\Delta t(7)$ between each pair of diameter measurements and establishing the propagation velocity of the pressure wave (9). Next, this value is compared with an expression (11) of the form $c(D) = c(D, \alpha, \beta, \gamma, \ldots)$ which takes into account the physical behavior of the artery. This comparison permits one, following adjustment (12) based on a mathematical procedure for minimizing spreads, to calculate the parameters $\alpha, \beta, \gamma, \ldots$ of the relation given hereinabove. By replacing the parameters $\alpha, \beta, \gamma, \ldots$ by their values in a relation (10) $D(p) = D(p, \alpha, \beta, \gamma, \ldots)$ and in employing the measurement results from a diameter sensor, one may deduce the blood pressure value $p(t)$ at each instant of the cardiac cycle. The blood pressure value together with the corresponding value of the artery diameter permit tracing a pressure-diameter curve (14) by means of which the mechanical properties of the artery may be measured.

6 Claims, 5 Drawing Sheets

METHOD FOR DETERMINING THE ARTERIAL BLOOD PRESSURE IN A NON-INVASIVE MANNER

FIELD OF THE INVENTION

This invention concerns a method for determining at each instant the blood pressure p(t) in an artery at a given point of its course and an arrangement for carrying out this method.

BACKGROUND OF THE INVENTION

It is known that arterial compliance which is the variation in the cross-section of the artery for a corresponding variation of the pressure reflects the elastic behaviour of the artery. This compliance is considered as indispensable to good knowledge of the physiology, the physiopathology and the therapy of the arterial system. This compliance is a function of the arterial pressure and in order to establish it one thus needs the instantaneous relationship which exists between the pressure and the diameter at a given point of the artery.

Propositions for measuring the pressure-diameter relationship have already been advanced, for example in the study presented on pages 789 to 793 of the review Arch. Mal. Coeur, Nr. 6, 1987, where the visco-elastic behaviour of the aorta was analyzed in a conscious dog. The visco-elastic response of the aorta to the administration of hormones is observed in the cited study by analyzing the pressure-diameter relationship of the aorta. This relationship is established by means of a microsensor for pressure which may be calibrated in situ and introduced through the left humeral artery and placed in the light of the descending aorta and of two piezoelectric crystals of 4 mm diameter diametrally attached in the envelope of the proximal descending aorta.

The means which have just been suggested have an invasive character, i.e. they affect the integrity of the organs in which they intervene. In respect of the human body, one prefers to employ sensors enabling non-invasive measures, such sensors remaining placed at the surface of the artery to be measured without any penetration into the surrounding tissues.

Non-invasive sensors enabling the continuous measurement of blood pressure are known. In particular, there may be mentioned the photoplethysmograph sold by the Ohmeda Company, 3030 Airco Drive, Madison, Wis., USA and bearing the registered trademark "finapres" (for finger arterial pressure). As indicated, the apparatus measures the blood pressure at the end of a finger according to the method described in the article "Effects of Peripheral Vasoconstriction on the Measurement of Blood Pressure in a Finger" in the review Cardiovascular Research, 1985, 19, 139-145.

Non-invasive sensors enabling the measurement of the arterial diameter are likewise known. In particular reference is made to the apparatus employed in the patent document U.S. Pat. No. 4,370,985 which enables measurement of the diameter of the artery by sending an ultrasonic wave on to the artery and measuring the echo sent back by the artery walls. This diameter measurement may be brought about on superficial arteries, for instance the humeral artery or the radial artery.

From the brief description of presently known sensors which has just been given hereinabove, it is apparent that it is not possible to measure non-invasively the pressure in every artery other than that of the finger and the diameter of said artery at the same place in a manner such that the relationship or curve pressure-diameter exhibits a systematic hysteresis. This is due to the fact that the speed of propagation of the pressure wave being finite, the variations of pressure measured downstream exhibit a certain delay relative to the corresponding variations of the diameter. This delay is evidently more substantial when the distance which separates the two measurement sites is increased.

SUMMARY OF THE INVENTION

To overcome this difficulty, the method and the arrangement of this invention propose to determine the blood pressure at the same location where the arterial diameter is measured and this by employing only two diameter sensors for the artery which are placed on the skin close to one another, these sensors enabling the deduction from the data which they supply of the value of the blood pressure. For this the method employed in the present invention is characterized by the fact that it includes the following succession of steps:

a) measuring non-invasively and simultaneously during at least one cardiac cycle a first diameter $D_1(t)$ of the artery at a first location and a second diameter $D_2(t)$ of the artery at a second location, said first and second locations being separated by a distance $\Delta x$, b) memorizing at successive instants of the cardiac cycle pairs of values each including a value $D_1(t)$ of said first diameter and a value $D_2(t)$ of said second diameter, the value of the diameter $D_2(t+\Delta t)$ such that $D_2(t+\Delta t) = D_1(t)$ in order thus to determine the time delay $\Delta t(d)$ between the diameter measurements of each of these pairs, d) calculating on the basis of said delay $\Delta t(D)$ and of each value of the first diameter $D_1(t)$ initially memorized during step b) the propagation velocity $c(D)$ of the pressure wave generated by the cardiac function in taking into account said distance $\Delta x$ by means of the relation $c(D) = \Delta x/\Delta t(D)$, e) choosing a mathematical relationship $D(p)=D(p, \alpha, \beta, \gamma, \ldots)$ which takes the behaviour of the artery into account, f) determining an algebraic expression $c(D)=c(D, \alpha, \beta, \gamma, \ldots)$ expressing the theoretical propagation velocity of the pressure wave as a function of the diameter from the preceding mathematical relationship chosen in step e), g) calculating by a mathematical adjustment method on the propagation velocity values obtained during step d) the parameters $\alpha, \beta, \gamma, \ldots$ from the algebraic expression previously obtained in step f), and h) calculating the blood pressure p(t) for each value of first diameters $D_1(t)$ previously memorized in step b) in replacing the parameters $\alpha, \beta, \gamma, \ldots$ of the mathematical relationship $d(p)=D(p, \alpha, \beta, \gamma, \ldots)$ chosen in step e) by their values.

It is also a purpose of this invention to provide an arrangement for practising the method as set forth hereinabove and this by means of two diameter sensors, a calculator and a visualization screen.

The invention will now be better understood in the light of the description to follow given by way of example and making reference to the drawings.

DESCRIPTION OF THE PREFERRED EMBODIMENT

Figure 1:
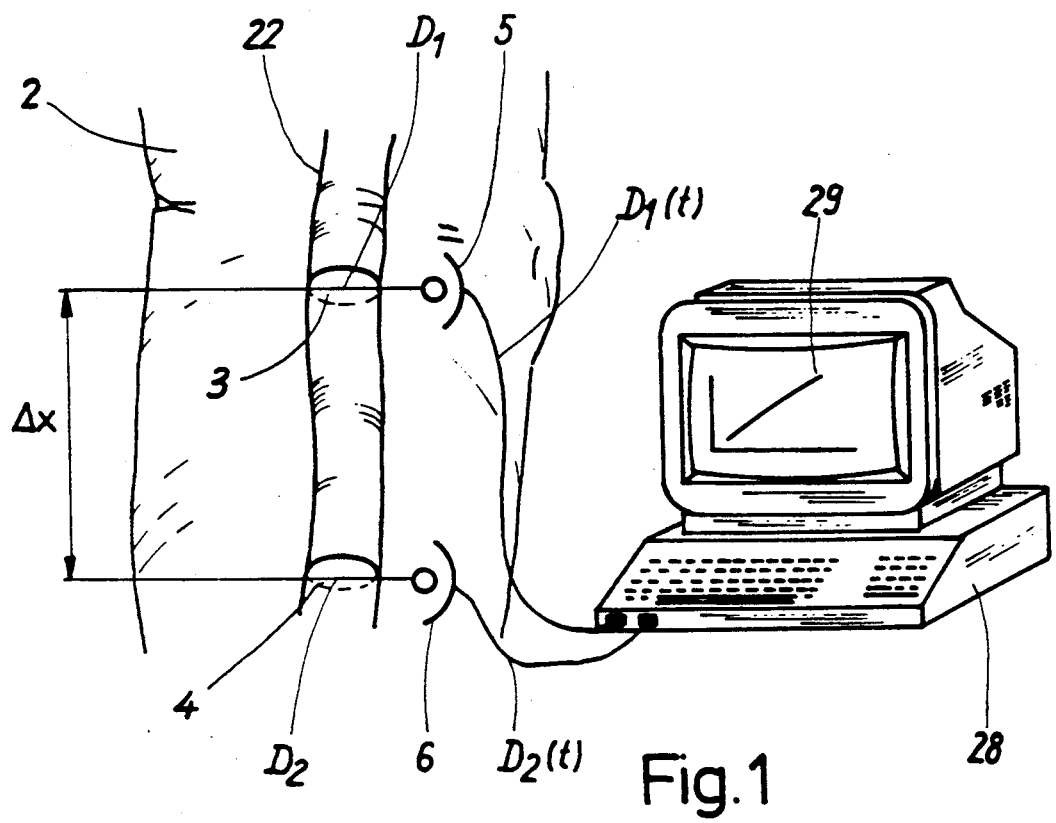
FIG. 1 is a schematic view of the measurement arrangement according to the invention showing an artery of the arm, two diameter sensors being arranged on the skin in proximity to said artery and a calculator provided with a visualization screen.
Figure 7:
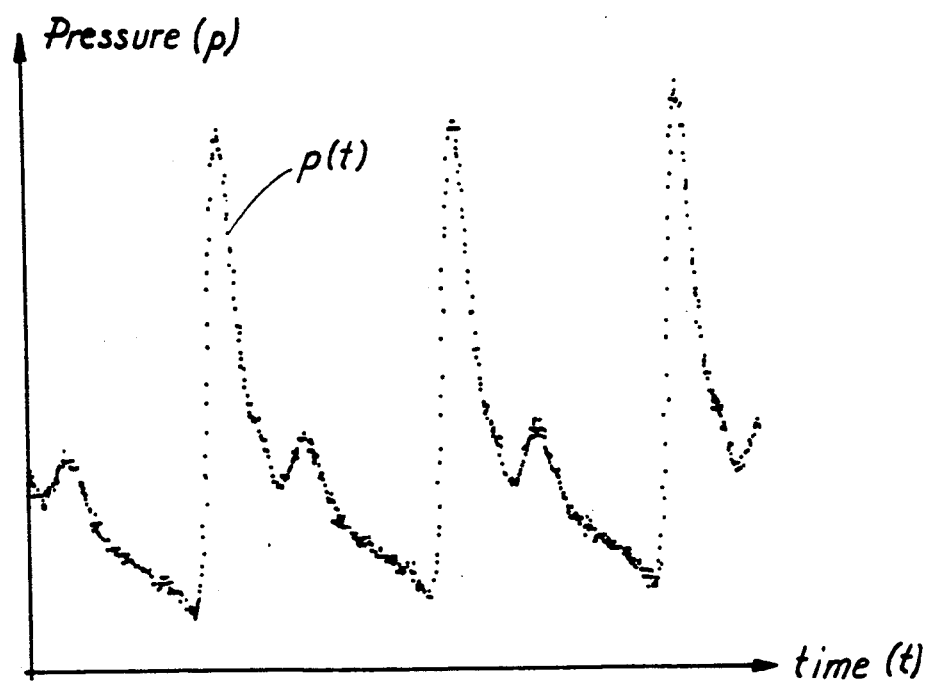
FIG. 7 is a diagram showing the arterial pressure as a function of time, this diagram resulting from that of FIG. 6.

On FIG. 1 there has been shown a length of surface artery 22 confined in an arm 2. This artery may be for instance the humeral artery. At a first location 3 on this artery there is measured the diameter $D_1(t)$ and at a second location 4 the diameter $D_2(t)$. The locations 3 and 4 are separated by a distance $\Delta x$. The sensors employed for this measurement are placed on the arm of the patient and symbolized on the figure by references 5 and 6. It thus concerns non-invasive measurements which do not require any introduction into the arm and the sensors employed to this end are of the ultrasonic emission type capturing the echoes from the walls of the artery as has been mentioned hereinabove. The signals $D_1(t)$ and $D_2(t)$ issuing respectively from sensors 5 and 6 are transmitted to a calculator 28 for processing. The calculator is completed by a visualization screen 29. The measurements take place during at least one cardiac cycle.

Figure 10:
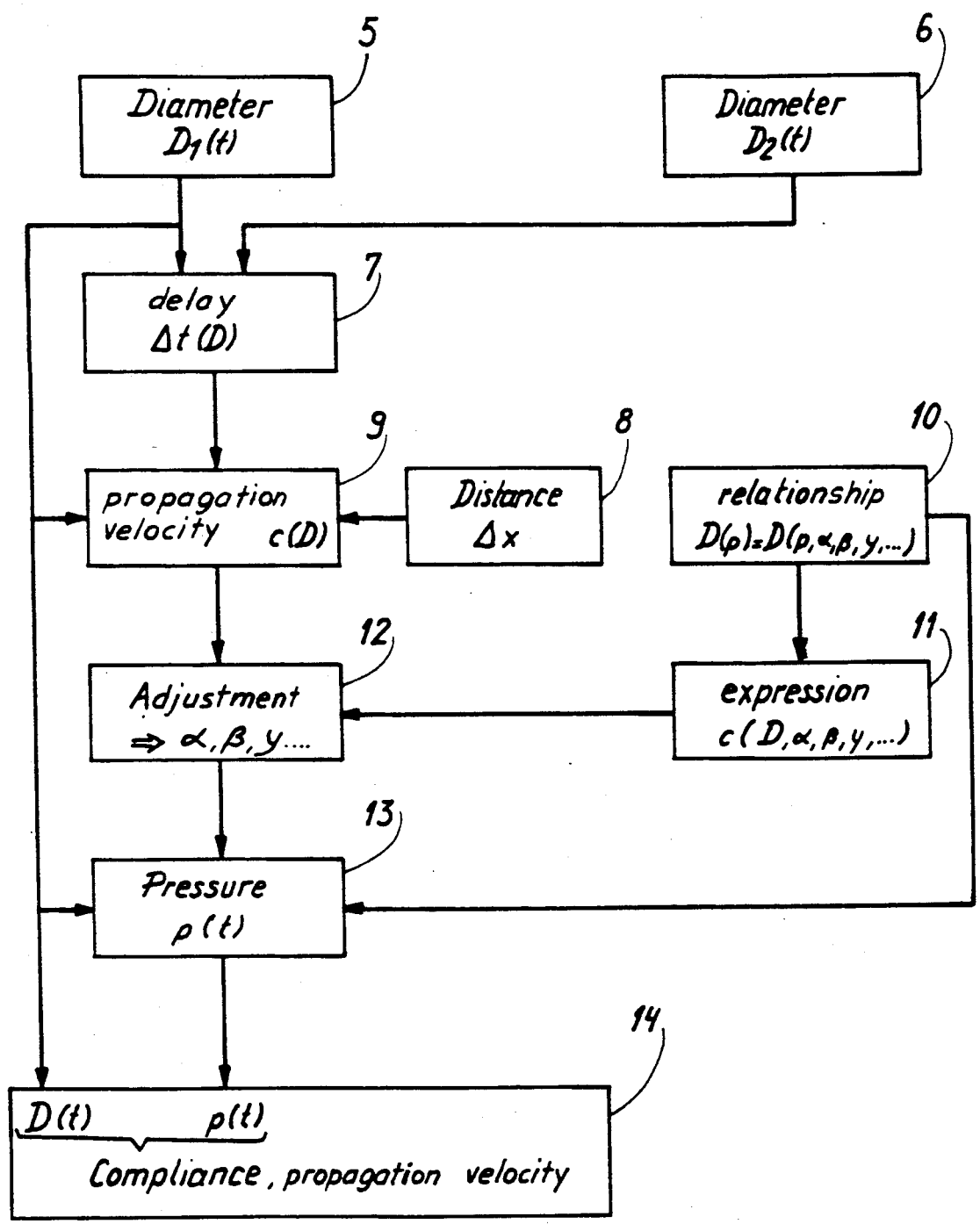
FIG. 10 is a flow chart showing how the various steps of the method according to the invention are connected together.

By means of the arrangement which has just been described, the method according to the invention for determining the blood pressure p(t) of an artery at a given point of its course will now be explained by means of the flow chart of FIG. 10 and the various diagrams shown on FIGS. 2 to 7.

Figure 2:
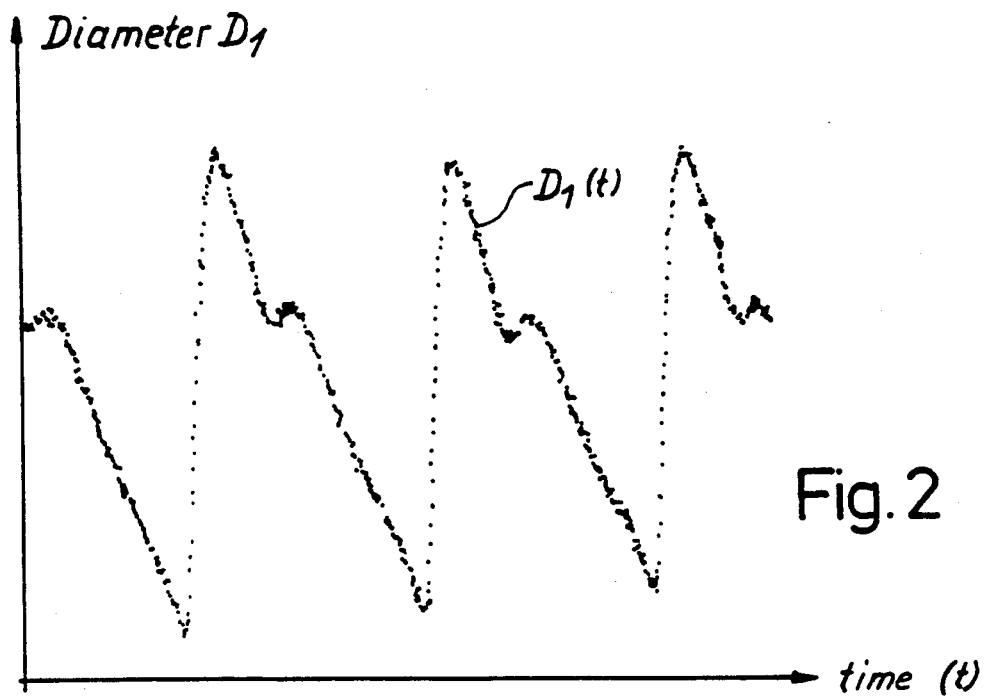
FIG. 2 is a diagram showing the signal $D_1(t)$ captured by the first diameter sensor as shown schematically on FIG. 1.
Figure 3:
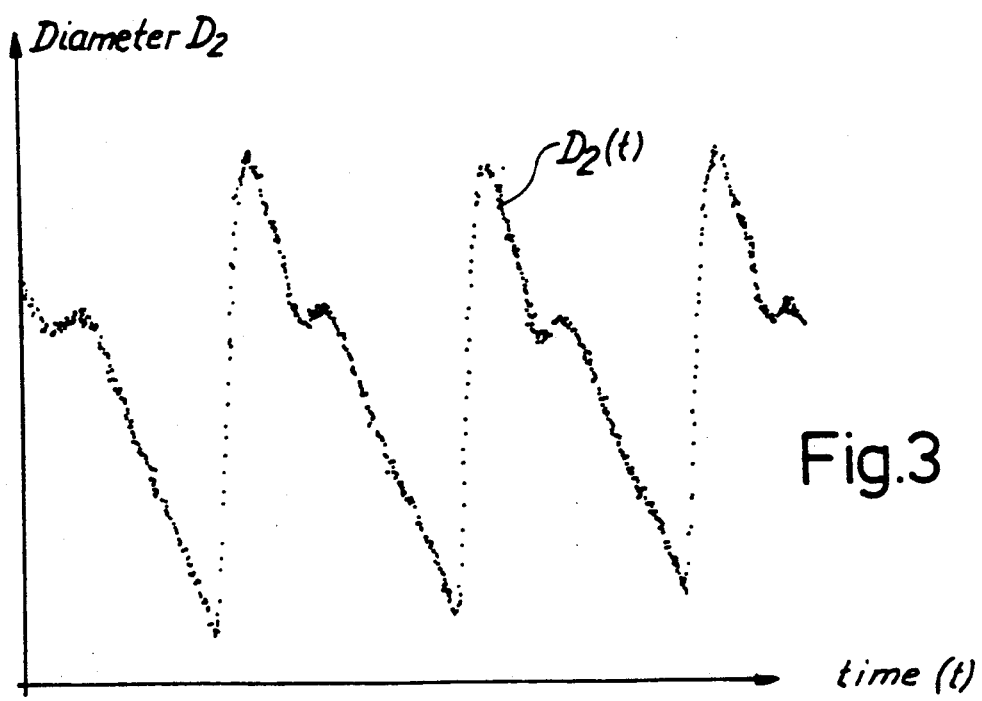
FIG. 3 is a diagram showing the signal D (t) captured by the second diameter sensor as schematically shown on FIG. 1.

FIG. 2 shows the signal $D_1(t)$ coming from sensor 5. The diagram shows the variation of the diameter $D_1$ of the artery as a function of time over about three cardiac cycles. FIG. 3 shows the signal $D_2(t)$ coming from captor 6. In the same manner, this diagram shows the variation of the diameter $D_2$ of the artery as a function of the time t over approximately three cardiac cycles. Thus, for a same time value $t_1$, for instance, one assembles a pair of diameter values $D_1(t_1)$ and $D_2(t_1)$ and continues thus thereafter for other time values.

Figure 4:
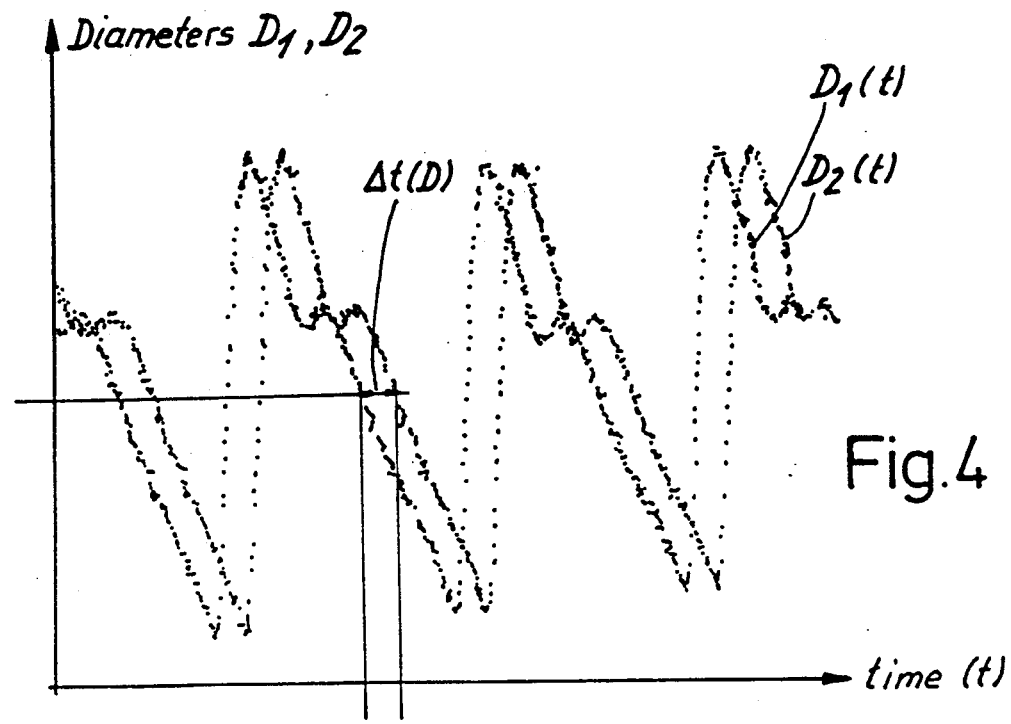
FIG. 4 is a diagram where the signals of FIGS. 2 and 3 have been superposed with a common time scale.
Figure 5:
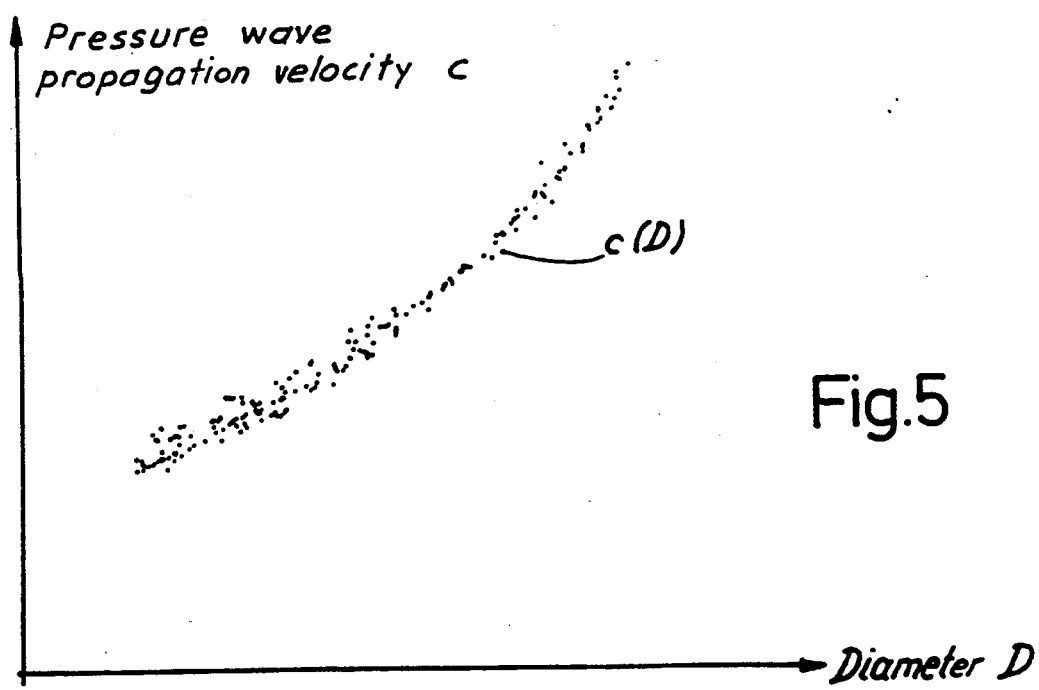
FIG. 5 is a diagram showing the propagation velocity of the pressure wave in the artery as a function of the arterial diameter.
Figure 6:
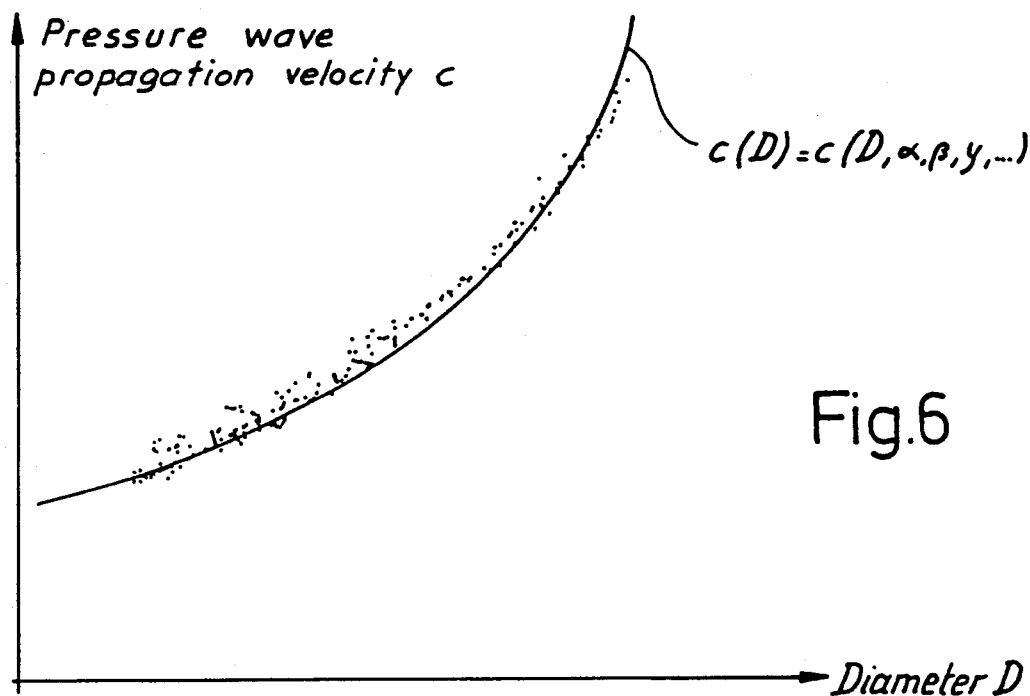
FIG. 6 is a diagram showing a curve resulting from an adjustment brought about on the set of points of the diagram of FIG. 5.

Next there is memorized (blocks 5 and 6 of the flow chart of FIG. 10), in calculator 28, in successive instants of the cardiac cycles, the pairs of values thus measured and one seeks the value of the diameter $D_2(t + \Delta t)$ such that $D_2(t+\Delta t) = D_1(t)$. The operation is shown in the diagram of FIG. 4 which is a superposition of the diagrams of FIGS. 2 and 3. This operation thus permits determination of the time delay $\Delta t(D)$ existing between the measurements of diameters of each of the memorized pairs. This delay, which is a function of the diameter D of the artery, is calculated and stored in block 7 of the flow chart of FIG. 10.

Next one calculates from the delay $\Delta t$ (D) and from each value of the first diameter $D_1(t)$ measured on block 5 of the flow chart, the propagation velocity c(D) of the pressure wave generated by the cardiac function by means of the relationship $c(D) = \Delta x / \Delta t(D)$, $\Delta x$ being the distance separating sensors 5 and 6. This calculation is symbolized by block 9 of the flow chart of FIG. 10 and the distance $\Delta x$ is stored in block 8 shown on the same flow chart. It will here be noted that the distance $\Delta x$ may be chosen on the order of 2 cm, this permitting a clear differentiation of the curves $D_1(t)$ and $D_2(t)$. With this order of magnitude, the time spread is in the order of a millisecond. The propagation velocity of the pressure wave c(D) is graphically shown on FIG. 5.

One will now choose a mathematical relationship $D(p) = D(p, \alpha, \beta, \gamma, \ldots)$ taking into account the behaviour of the artery. This relationship, which is stored in block 10 of the flow chart of FIG. 10, is given by experience. It could be of the exponential form:

$$p = \alpha e^{\frac{\beta \pi D^2}{4}}$$

or again of a form given in the review J. Biomechanics, Vol. 17, Nr. 6, pages 425–435, 1984 and which is written:

$$S = \alpha[\tfrac{1}{2} + \tan^{-1}[(p-\beta)/\gamma]/\pi$$

where $$S = \frac{\pi D^2}{4} .$$

is the cross-section of the artery, $\alpha$ is its maximal area, p is the transmural pressure, $\beta$ is the pressure at which compliance is maximal, and $\gamma$ is the half width pressure. It will be noted that in the numerous relationships proposed in the literature, the number of parameters $\alpha, \beta, \gamma, \ldots$ is variable.

The next stage in the method according to the invention consists in determining an algebraic expression c(D) c(D, $\alpha, \beta, \gamma, \ldots$) which expresses the theoretical velocity of propagation of the pressure wave as a function of the diameter starting from the mathematical relationship as mentioned hereinabove. This expression may be obtained in different manners, for instance by employing the expression $$c(p) = \sqrt{\frac{S}{\rho} \cdot \frac{dp}{dS}} \text{ where } S = \frac{\pi D^2}{4} ,$$

where $\rho$ is the blood density and where $$\frac{dp}{dS}$$

is the derivative of the pressure by the cross-section. It will be noted that the expression c(p) is known from the study of arterial haemodynamics. This stage is symbolized by block 11 of the flow chart of FIG. 10.

An important step in the method according to the invention consists then in employing the values of the propagation velocity c(D) contained in block 9 and the theoretical values of the propagation velocity c(D, $\alpha$, $\beta$, $\gamma$, ...) in order to calculate the parameters $\alpha$, $\beta$, $\gamma$, ... by employing a mathematical method of adjustment or routine known from the prior art, for instance the least squares method. Other methods are possible and are described in detail in the work "Numerical Recipes" published by the Press Syndicate of the University of Cambridge 1986. Very generally, it concerns a standard mathematical method of minimization of spreads. This adjustment (or "fit") is present at the output of block 12 of the flow chart of FIG. 10. The result of this adjustment is shown by the full curve on FIG. 6.

Finally, in replacing by their values the parameters $\alpha$, $\beta$, $\gamma$, ... obtained in the preceding stage in the relationship $D(p) = D(p, \alpha, \beta, \gamma, ...)$ contained in block 10, one may calculate the blood pressure p(t) for each value of the first diameters $D_1(t)$ obtained previously at the stage symbolized by block 5. The configuration of this pressure as a function of time is represented on the diagram of FIG. 7 and its values are present on block 13 of the flow chart of FIG. 10.

Thus, one has achieved the purpose set forth in the objective of the present invention, namely determination of the blood pressure at each instant of the cardiac cycle, such determination being based on the single measurement of the arterial diameter at two distinct locations in its course.

This measurement may be effected on the humeral artery as has been mentioned hereinabove. It could also be effected at other locations of any surface artery whatsoever, for instance in the leg or the neck.

Figure 8:
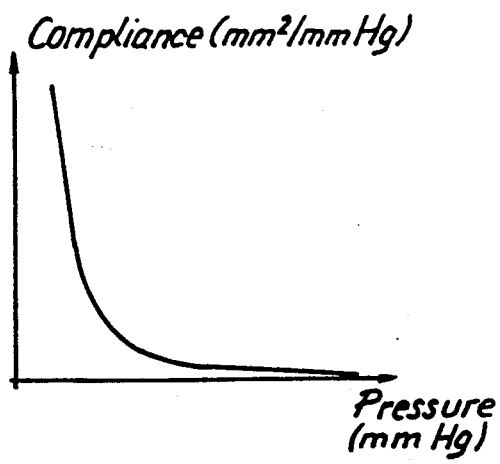
FIG. 8 is a diagram representing the compliance of the artery as a function of the pressure.
Figure 9:
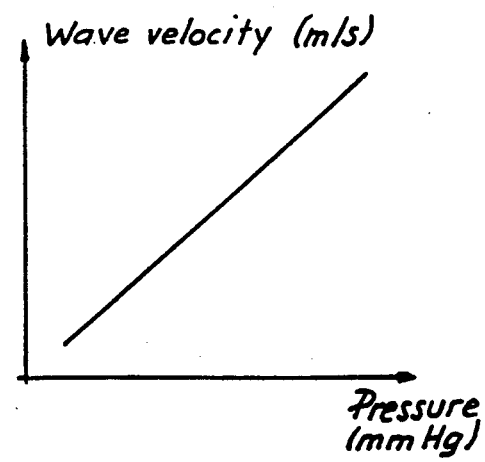
FIG. 9 is a diagram representing the speed of propagation of the pressure wave as a function of the pressure.

From the values of the pressure p(t) and the diameter $D_1(t)$ at a single location 3 of the artery, it is easy then to establish the relationship pressure–diameter D(p) of said artery. From this relationship one may then obtain the value of the compliance as a function of the pressure (FIG. 8) and of the speed of propagation of the pressure wave c(p) (FIG. 9).

It will be mentioned further that all the stages of the method according to the invention as well as the calculations which appear in the flow chart of FIG. 11 may be effected by means of a computer available on the market, for instance by means of the Olivetti apparatus M28. In the same manner, the visualization screen 29 enables, at the request of the practitioner, the showing of any graphical presentation whatsoever in the course of or at the end of the procedure.

What we claim is:
1. A method for determining at each instant the blood pressure p(t) in an artery at a given point in its course including the following succession of steps:
   a) measuring non-invasively and simultaneously during a cardiac cycle a first diameter $D_1(t)$ of the artery at a first location and a second diameter $D_2(t)$ of the artery at a second location, said first and second locations being separated by a distance $\Delta x$, to produce signals representing said diameters, said measuring of said first and second diameters comprising directing ultrasonic waves toward said artery at said first and second locations and sensing echoes of said waves reflected from a wall of said artery to produce electrical signals representing said diameters,
   b) storing in a memory device at successive instants of the cardiac cycle pairs of values of said signals each pair including a value $D_1(t)$ of said first diameter and a value $D_2(t)$ of said second diameter,
   c) for the diameter pairs thus stored, seeking the value of the diameter $D_2(t+\Delta t)$ such that $D_2(t+\Delta t) = D_1(t)$ in order thus to determine the time delay $\Delta t(D)$ between the diameter measurements of each of these pairs,
   d) calculating on the basis of said time delays $\Delta t(D)$ and of each value of the first diameter $D_1(t)$ initially stored during step b) the propagation velocity c(D) of the pressure wave generated by the cardiac function in taking into account said distance $\Delta x$ by means of the relation $c(D) = \Delta x / \Delta t(D)$,
   e) choosing a mathematical relationship $D(p) = D(p, \alpha, \beta, \gamma, ...)$ which takes the behavior of the artery into account,
   f) determining an algebraic expression $c(D) = c(D, \alpha, \beta, \gamma, ...)$ expressing the theoretical propagation velocity of the pressure wave as a function of the diameter from the preceding mathematical relationship chosen in step e),
   g) calculating by a mathematical adjustment method on the propagation velocity values obtained during step d) the parameters $\alpha$, $\beta$, $\gamma$, ... from the algebraic expression previously obtained in step f), and
   h) calculating the blood pressure p(t) for each value of first diameters $D_1(t)$ previously stored in step b) in replacing the parameters of the mathematical relationship $d(p) = D(pm\ \alpha, \beta, \gamma ...)$ chosen in step e) by their values.

2. A method as set forth in claim 1 wherein, in order to determine the algebraic expression $c(D) = (D, \alpha, \beta, \gamma. ..)$ of step f), the expression $$c(p) = \sqrt{\frac{S}{\rho} \cdot \frac{dp}{dS}} \quad \text{is employed, where } S = \frac{\pi D^2}{4}$$

and where $\rho$ is the blood density.

3. The method as claimed in claim 1 and further comprising the step of displaying said calculated blood pressures p(t) on a visualization screen.

4. The method as claimed in claim 1 and further comprising the step of simultaneously displaying said calculated blood pressures p(t) calculated during said cardiac cycle as a curve on a visualization screen.

5. A method for non-invasively determining at each instant in a cardiac cycle blood pressure values representing the blood pressure in an artery at a given point in its course, said method comprising:
   disposing first and second sensors outside said artery at first and second points separated by a distance X along the course of said artery, said sensors producing output signals representing the diameters of said artery at said first and second points, respectively;
   repeatedly and simultaneously sampling said output signals from said sensors over an interval including at least one cardiac cycle to produce pairs of values representing the sensed diameters at said first and second points;
   storing said pairs of values in a computer memory;
   determining, from said stored pairs of values, the delay between a time said first sensor produces an output signal of a given magnitude and a time said second sensor produces an output signal of the same magnitude, and producing a delay signal representing said delay;

determining from said delay signal and said value representing said distance X, the actual propagation velocity between said first and second points of a pressure wave generated by the cardiac function;

choosing a mathematical relationship $D(p) = D(p, \alpha, \beta, \gamma...)$ where $\alpha, \beta, \gamma...$ are parameters expressing behavior of the artery and p represents pressure;

determining from said mathematical relationship the theoretical velocity of propagation of said pressure wave as a function of the diameter of the artery;

determining from said theoretical velocity of propagation and said actual propagation velocity, numerical values of said parameters; and, calculating said blood pressure values by substituting said numerical values of said parameters in said mathematical relationship.

6. The method as claimed in claim 5 and further comprising the step of simultaneously displaying said calculated blood pressure values as a curve on a visualization screen.

* * * * *